United States Patent
Hsu

(10) Patent No.: US 8,647,846 B2
(45) Date of Patent: Feb. 11, 2014

(54) CONTAINER AND METHOD FOR PRODUCTION OF BIOMEMBRANE

(76) Inventor: Connie Hui-Ju Hsu, Yung-Kang (TW)

( * ) Notice: Subject to any disclaimer, the term of this patent is extended or adjusted under 35 U.S.C. 154(b) by 1325 days.

(21) Appl. No.: 11/987,584

(22) Filed: Dec. 3, 2007

(65) Prior Publication Data

US 2008/0286839 A1 Nov. 20, 2008

(30) Foreign Application Priority Data

May 11, 2007 (TW) .............................. 96116762 A

(51) Int. Cl.
 *C12P 19/06* (2006.01)
 *C12M 1/22* (2006.01)
(52) U.S. Cl.
 USPC ........................................ 435/104; 435/305.1
(58) Field of Classification Search
 None
 See application file for complete search history.

(56) References Cited

U.S. PATENT DOCUMENTS

| 5,605,836 A | 2/1997 | Chen et al. |
| 6,071,727 A * | 6/2000 | Bungay et al. ................ 435/101 |
| 6,204,051 B1 | 3/2001 | Copeland et al. |
| 6,936,463 B1 | 8/2005 | Chen et al. |
| 2006/0286434 A1 * | 12/2006 | Evans et al. ..................... 429/42 |
| 2007/0026516 A1 | 2/2007 | Martin et al. |

FOREIGN PATENT DOCUMENTS

| GB | 2413562 A | 2/2005 |
| TW | 083110227 | 11/1994 |
| TW | 200815601 A | 4/2008 |

\* cited by examiner

*Primary Examiner* — Robert A Zeman
(74) *Attorney, Agent, or Firm* — Bacon & Thomas, PLLC

(57) ABSTRACT

A method and a container for production of a biomembrane are disclosed in the present invention. The biomembrane produced in the method and in the container of the present invention can be processed into a mask, wherein processes for changing the shape of the biomembrane are unnecessary. The mask produced from the biomembrane can be efficient to maintain the skin, and to supply the moisture thereto.

20 Claims, 6 Drawing Sheets

CONTAINER AND METHOD FOR PRODUCTION OF BIOMEMBRANE

BACKGROUND OF THE INVENTION

1. Field of the Invention

The present invention relates to a container and a method for production of a biomembrane and, more particularly, to a container and a method of using microorganisms to produce polymer forming a biomembrane.

2. Description of Related Art

On the market, there are various masks for the purpose of satisfying the need to maintain human skin condition. In general, non-woven fabric is used as a base of masks for containing various cosmetics and medicines. This kind of non-woven fabric is not a cloth knit by thread, but it is a fiber material without being knit by textile processes. Therefore, the non-woven fabric has properties of air permeability, hygroscopicity, durability, drug tolerance, insulativity, and so forth. However, due to good hygroscopicity of the non-woven fabric, various active cosmetics and medicines contained therein are exposed in a two-way direction. Hence, the active cosmetics and medicines easily decompose or evaporate so that the masks can not exhibit all their functions.

Currently, a biomembrane made of polymer produced by microorganisms has been developed. This kind of biomembrane can be processed into, for example, dietary fibers for eating, masks for skin maintenance, and so on. The biomembrane has high water absorption so as to carry large amounts of nutrients. If the biomembrane is manufactured into a mask, the mask can supply nutrition for skin. Besides, the biomembrane has lots of advantageous properties of, for example, having free functional groups which can absorb dirt of skin.

In order to avoid covering organs such as the eyes, the nose, the mouth etc. on the face of the user otherwise resulting in being incapable of watching, smelling, eating, or talking, masks made of conventional non-woven fabric or made of biomembrane are all processed to form predetermined holes so that the user aforementioned requirements can be satisfied. However, formation of the predetermined holes needs die cutting that incurs complex steps of manufacturing and edge impairment of masks or predetermined holes. Accordingly, the yield of the masks is leveled down so that the costs of the production for the masks are raised.

SUMMARY OF THE INVENTION

In view of the abovementioned shortcomings, one object of the present invention is to provide a container for production of a biomembrane which does not need the shape thereof to be changed. Besides, the containers can be stacked up vertically so as to get more horizontal space for production. The vertically stacked-up containers still have good airflow thereinto.

Another object of the present invention is to provide a method for production of a biomembrane. Through microbial strains naturally producing polymers such as polysaccharide, polyglutamate etc. in a predetermined container, a biomembrane can be formed to have a shape according to the predetermined container. Additionally, when the biomembrane is processed into a mask, no processes for changing the biomembrane are required. Therefore, the yield of the masks is raised. In another way, the manufactured mask can be used for skin maintenance and moisture supply to skin.

In order to achieve the object, a container for culturing a biomembrane is provided in the present invention, which includes a bottom plate; a sidewall disposed on the bottom plate and surrounding the periphery of the bottom plate to form an inner space; and at least one protrusion locating on the surface of the bottom plate.

In the abovementioned container, the sidewall has a recessive brink and a prominent brink, the recessive brink is at the upper part of the sidewall, and the prominent brink is at the lower part of the sidewall. Besides, plural holes are defined in the upper surface of the sidewall, and plural pins corresponding to the holes are placed on the lower surface of the sidewall. If the containers are vertically stacked up one by one, horizontal space for culturing can be economized. Additionally, through the pins inserting into the holes or the prominent brink corresponding to the recessive brink, the containers stacked up can be more stable and not easily be loosened to collapse. The depth of the holes can be equal to or less than the height of the pins. Furthermore, the cross-section of the upper part of the pins can be equal to or greater than that of the pins.

Moreover, plural recesses locate on the outer surface of the sidewall, and those are not limited in any shape. The shape of the sidewall surrounding the periphery of the bottom plate is not limited to, but preferably is circular, elliptic, polygonal, irregular, or oval. The protrusion is not limited to, but preferably is columnar, taper, or sheeted. Additionally, the protrusion can be placed in any position of the container. Preferably, the protrusion can be arranged by way of corresponding to the facial features of a person, i.e. eyes, nose, mouth and so forth. The bottom plate can be planar or not planar, the latter means the bottom plate is a cambered surface.

In the abovementioned container, the protrusion can be formed by indenting from the outside surface of the bottom plate to the inside surface of the bottom plate. Hence, the material of the container can be economized by way of the above-mentioned method. Besides, the material of the container is not limited to, but preferably is transparent or non-transparent organic material (such as PVC, PP, and PE) or an anti-oxidative metal. The surface of the container can be selectively coated with PEP.

Furthermore, the present invention also discloses a method for production of a biomembrane, which includes the following steps: (a) providing a first medium and a microbial strain therein, and shaking them to form a seed culture; (b) putting the seed culture into a container having a second medium, and the container comprising a bottom plate, a sidewall disposed on the bottom plate and surrounding the periphery of the bottom plate, and at least one protrusion locating on the surface of the bottom plate to form an inner space; and (c) culturing the seed culture until a biomembrane having a predetermined thickness is formed.

In the abovementioned method of the present invention, the microbial strain preferably is *Acetobacter* spp., *Gluconacetobacter* spp., *Xanthomonas* spp., or *Bacillus* spp. More preferably, the microbial strain of the *Acetobacter* spp. is *A. xylinum*; the microbial strain of the *Gluconacetobacter* spp. is *G. xylinus* subsp. *Xylinus*, or *G. Hansenii*; the microbial strain of the *Xanthomonas* spp. is *X. camperastris*; and the microbial strain of the *Bacillus* spp. is *B. substilis* var Natto.

Additionally, the first medium and the second medium comprise a carbohydrate, an N-containing compound, a mineral, and a growth cofactor. The content of the carbohydrate, the N-containing compound, the mineral, and the growth cofactor preferably is 1~30%, 0.16%, 0.05~3%, and 0.05~2%, respectively. The carbohydrate is not limited to, but preferably is at least one selected from monosaccharide, disaccharides, polysaccharides, or carboxyl-containing compounds. The N-containing compound is not limited to, but preferably is at least one selected from yeast extract, peptone, soybean powders, or gelatin. The mineral is not limited to, but preferably is at least one selected from chloride salt, ammonium salt, sulfide salt, potassium salt, phosphate, magnesium salt, or sodium salt. The growth cofactor is not limited to, but preferably is at least one selected from vitamin, nicotinic acid, citric acid, or the derivatives thereof.

In order to obtain large-scaled seed culture for production, the method disclosed in the present invention can further comprise a step (a1): amplifying the seed culture to afford great amount of seed culture for mass production after the step (a) is achieved.

The biomembrane manufactured by the method of the present invention can be processed into a facial mask, an eye mask, a chested mask, or a lip mask. The above-mentioned masks can efficiently provide water to maintain skin condition. Additionally, these masks are not required to change their shape by subsequent steps because the biomembrane in the present invention can be formed in the final shape. Furthermore, the biomembrane of the present invention does not have shortcomings of conventional masks being required to change shape thereof. Hence, the biomembrane in the present invention can have good yield without impairment due to the process of changing shape.

Other objects, advantages, and novel features of the invention will become more apparent from the following detailed description when taken in conjunction with the accompanying drawings.

DETAILED DESCRIPTION OF THE PREFERRED EMBODIMENT

In the following examples, the microbial strain used in the present invention is *Acetobacter* spp., *Gluconacetobacter* spp., *Xanthomonas* spp., or *Bacillus* spp. In the *Acetobacter* spp., *A. xylinum* is used; in the *Acetobacter* spp., *G. xylinus* subsp. *Xylinus* ATTC 10821, *G. xylinus* subsp. *Xylinus* ATTC 700187, or *G. Hansenii* ATTC 23769 are used; in the *Xanthomonas* spp., *X. camperastris* is used; and in the *Bacillus* spp., *B. substilis* var Natto is used. In the above mentioned, although *A. xylinum* is not named as *G. xylinus*, they are the same microorganism.

The mediums used in the method of the present invention comprise a carbohydrate, an N-containing compound, a mineral, and a growth cofactor. In the following examples, the content of the carbohydrate is 1~30%; the content of the N-containing compound is 0.1~6%; the content of the mineral is 0.05~3%; and the content of the growth cofactor is 0.05~2%. Besides, at least one of monosaccharide, disaccharides, polysaccharides, and carboxyl-containing compounds is used as the carbohydrate; at least one of yeast extract, peptone, soybean powders, and gelatin is used as the N-containing compound; at least one of chloride salt, ammonium salt, sulfide salt, potassium salt, phosphate, magnesium salt, and sodium salt is used as the mineral; and at least one of vitamin, nicotinic acid, citric acid, and the derivatives thereof is used as the growth cofactor.

In the method of the present invention, which shape of the container is used is in view of the required biomembrane shape, for example, if a rectangular biomembrane is required, the cuboid container can be used, or if a circular biomembrane is required, the cylindrical container can be used. In the following examples, the container used therein is as shown in FIGS. 1a~4, but is not limited to. The container can be made of PVC, PP, PE, or antioxidative metals. Besides, the container can be selectively coated with PEP. PEP is a high molecular weight rust-preventing membrane, and that can prevent corrosive gas from permeating by coating the container and neutralizing the permeating corrosive gas.

Examples 1-30

About 1~5 loops of *A. xylinum* are transferred from the slant culture to a sterile liquid medium (as the following Table 1). The liquid medium is cultured for 13 days at 37° C. by shaking, and then amplified with 2~30-folds sterile liquid medium. This amplification can be performed for 1~2 days in a fermenting tank or a shaking incubator so as to obtain seed culture for large-scaled production.

TABLE 1

| Components | Content (%) |
| --- | --- |
| Glucose | 2 |
| Peptone | 1 |
| Yeast extract | 1 |
| Citric acid | 0.1 |
| Sodium biphosphate | 0.3 |

Figure 1A:
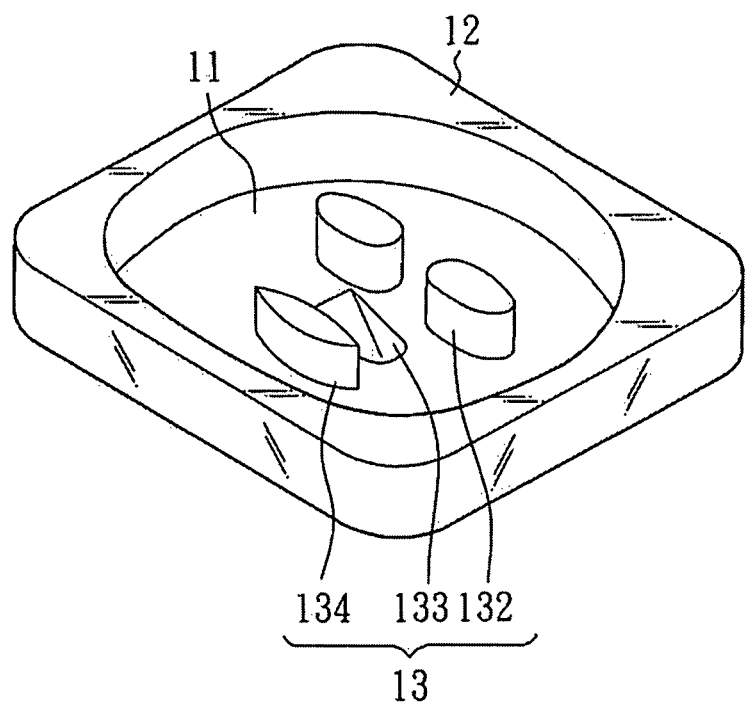
FIG. 1a is a perspective view of a container for production of a biomembrane in the present invention.

The container for culturing used in the present examples is shown in FIG. 1a. The container a bottom plate 11; a sidewall 12 disposed on the bottom plate 11 and surrounding the periphery of the bottom plate 11, wherein an inner space is surrounded by the sidewall 12 and the bottom plate 11; and at least one protrusion 13 locating on the surface of the bottom plate 11. The protrusion 13 mentioned above can be in any shape, for example, the first protrusion 132 is an elliptic cylinder; the second protrusion 133 is a cone; and the third protrusion 133 is a leaf-shaped pillar. Besides, the protrusion 13 can be placed in any location in accordance with the shape of the required biomembrane.

Figure 1B:
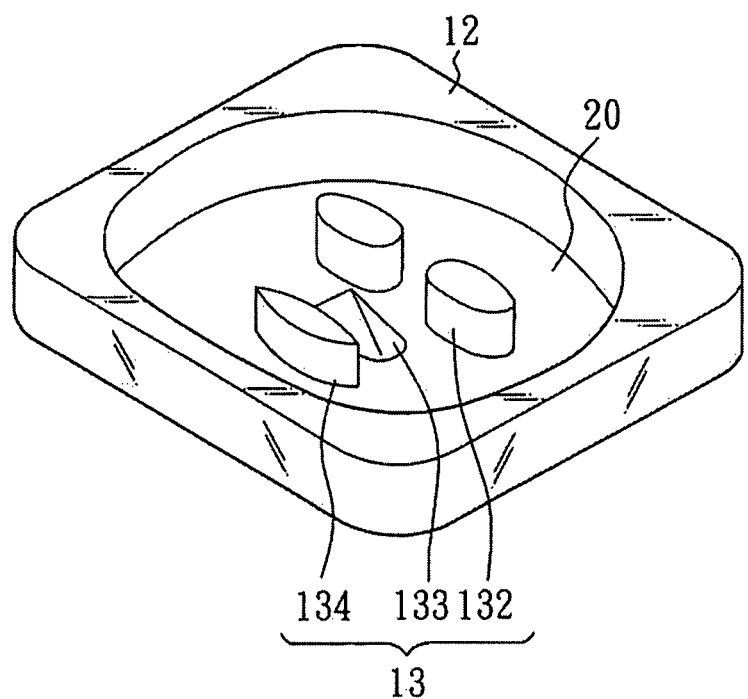
FIG. 1b is a perspective view of a container when production of a biomembrane occurs in the example of the present invention.
Figure 5:
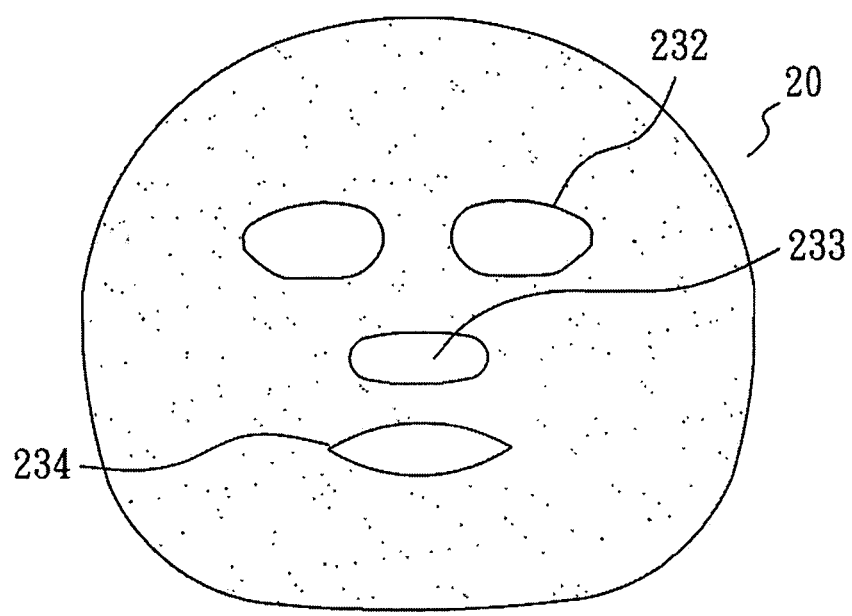
FIG. 5 is a top view of a biomembrane produced from the examples of the present invention.

As shown in FIG. 1b, about 1%~50% of the seed culture is mixed with the culture medium in Table 2 and that is cultured in the inner space of the above-mentioned container. A biomembrane 20 is formed in a shape according to that of the container. At a constant temperature, the biomembrane 20 is cultured until it has a predetermined thickness. Then, the biomembrane 20 is taken out. As shown in FIG. 5, the biomembrane 20 have several openings 232, 233, and 234 respectively corresponding to the first protrusion 132, the second protrusion 133, and the third protrusion 133.

TABLE 2

| Component (%) | Example | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Peptone | | | | | | | | 1 | | | | | | | |
| MgSO$_4$ | | | | | | | | 0.1 | | | | | | | |
| Yeast extract | | | | | | | | 1 | | | | | | | |
| CaCO$_3$ | | | 0 | | | | | 0.1 | | | | | 0.3 | | |
| Glucose | 2.5 | 5 | 10 | 20 | 30 | 2.5 | 5 | 10 | 20 | 30 | 2.5 | 5 | 10 | 20 | 30 |

| Component (%) | Example | | | | | | | | | | | | | | |
|---|---|---|---|---|---|---|---|---|---|---|---|---|---|---|---|
| | 16 | 17 | 18 | 19 | 20 | 21 | 22 | 23 | 24 | 25 | 26 | 27 | 28 | 29 | 30 |
| Peptone | | | | | | | | 1 | | | | | | | |
| MgSO$_4$ | | | | | | | | 0.1 | | | | | | | |
| Yeast extract | | | | | | | | 1 | | | | | | | |
| CaCO$_3$ | | | 0 | | | | | 0.1 | | | | | 0.3 | | |
| Glucose | 2.5 | 5 | 10 | 20 | 30 | 2.5 | 5 | 10 | 20 | 30 | 2.5 | 5 | 10 | 20 | 30 |

Figure 6:
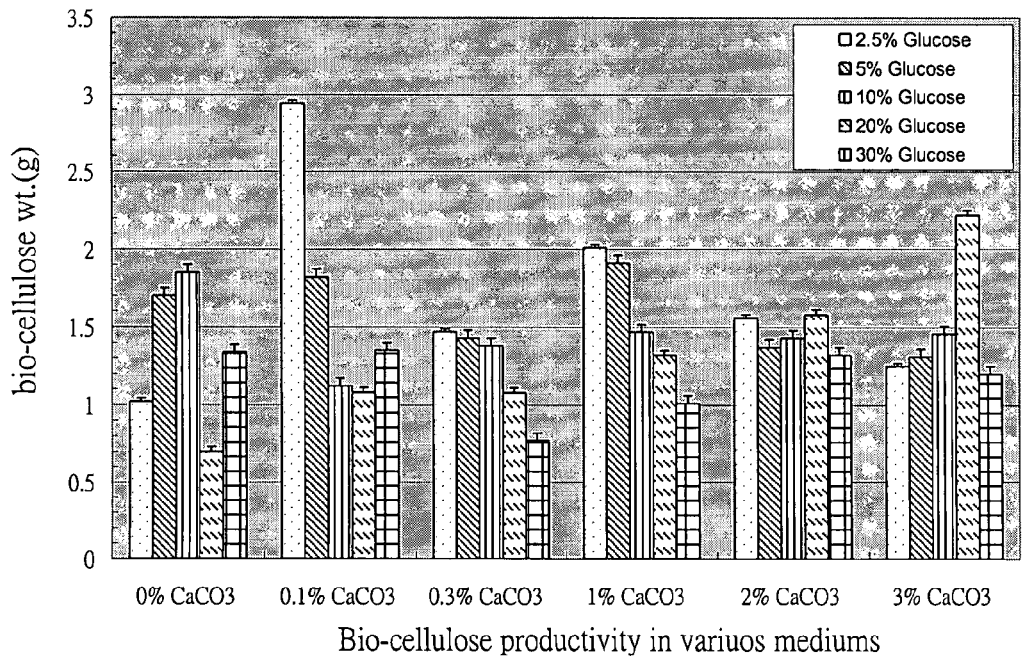
FIG. 6 is a chart of biocellulose production among examples 1 to 30 in the present invention.

Through tests of the examples 1~30, the result is shown in FIG. 6. In accordance with the formation weight of the biomembrane 20, the culture medium comprising 1% yeast extract, 0.1% CaCO$_3$, and 2.5% glucose can be an optimal medium to culture a biomembrane having an optimal production weight.

Examples 31~60

About 15 loops of *A. xylinum* are transferred from the slant culture to a sterile liquid medium (as Table 1 in Examples 1~30). The liquid medium is cultured for 13 days at 37° C. by shaking, and then amplified with 2~30-folds sterile liquid medium. This amplification can be performed for 1~2 days in a fermenting tank or a shaking incubator so as to obtain seed culture for large-scaled production.

Figure 2:
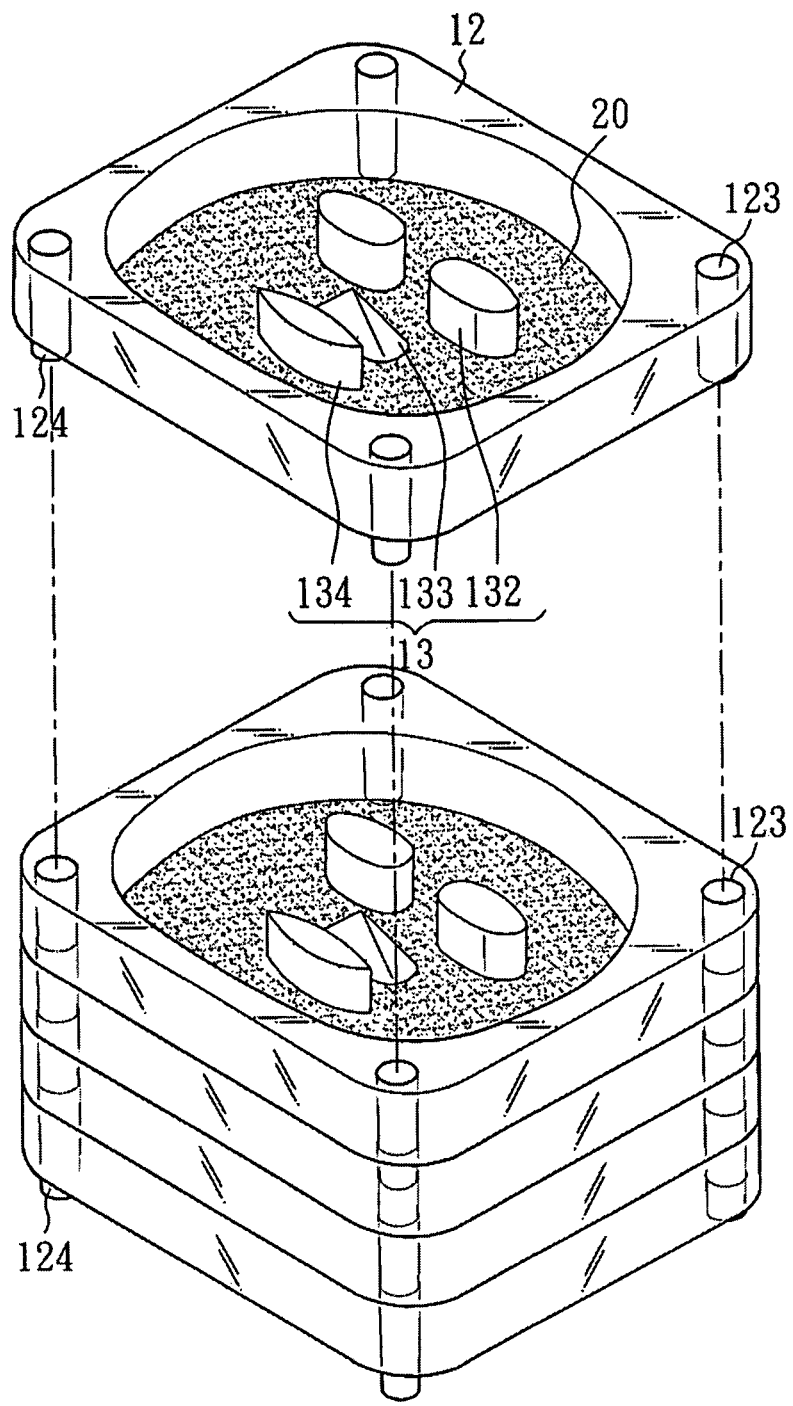
FIG. 2 is a perspective view of a container when production of a biomembrane occurs in the example of the present invention.

In the present examples, the container used therein is as shown in FIG. 2, and approximately is similar to the container shown in FIG. 1a. However, the container in the FIG. 2 has plural holes 123 through the upper surface of the sidewall 12, and plural pins 124 on the lower surface of the sidewall 12. The pins 124 are placed through corresponding holes 123.

About 1%~50% of the seed culture is mixed with the culture medium in Table 2 and that is cultured in the inner space of the above-mentioned container. Besides, the containers can be vertically stacked up one by one. Through the pins 124 inserting into the holes 123, the stacked up containers can become a stable vertical structure. Additionally, the stacked up containers does not easily collapse or become loosened. Hence, the horizontal space for production can be economized. A biomembrane 20 is formed in a shape according to that of the container. At a constant temperature, the biomembrane 20 is cultured until the biomembrane 20 have a predetermined thickness. Then, the biomembrane 20 as shown in FIG. 5 is taken out.

TABLE 3

| Component (%) | Example | | | | | | | | | | | | | | |
|---|---|---|---|---|---|---|---|---|---|---|---|---|---|---|---|
| | 31 | 32 | 33 | 34 | 35 | 36 | 37 | 38 | 39 | 40 | 41 | 42 | 43 | 44 | 45 |
| Peptone | | | | | | | | 1 | | | | | | | |
| MgSO$_4$ | | | | | | | | 0.1 | | | | | | | |
| Yeast extract | | | | | | | | 0.5 | | | | | | | |
| CaCO$_3$ | | | 0 | | | | | 0.1 | | | | | 0.3 | | |
| Glucose | 2.5 | 5 | 10 | 20 | 30 | 2.5 | 5 | 10 | 20 | 30 | 2.5 | 5 | 10 | 20 | 30 |

| Component (%) | Example | | | | | | | | | | | | | | |
|---|---|---|---|---|---|---|---|---|---|---|---|---|---|---|---|
| | 46 | 47 | 48 | 49 | 50 | 51 | 52 | 53 | 54 | 55 | 56 | 57 | 58 | 59 | 60 |
| Peptone | | | | | | | | 1 | | | | | | | |
| MgSO$_4$ | | | | | | | | 0.1 | | | | | | | |
| Yeast extract | | | | | | | | 0.5 | | | | | | | |
| CaCO$_3$ | | | 0 | | | | | 0.1 | | | | | 0.3 | | |
| Glucose | 2.5 | 5 | 10 | 20 | 30 | 2.5 | 5 | 10 | 20 | 30 | 2.5 | 5 | 10 | 20 | 30 |

Figure 7:
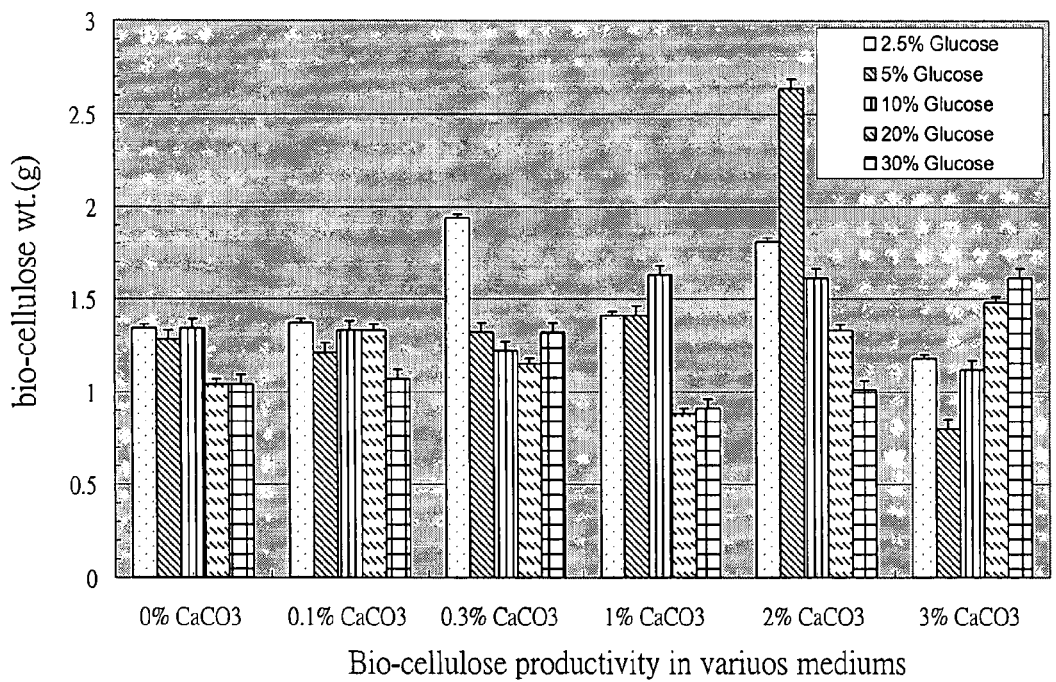
FIG. 7 is a chart of biocellulose production among examples 31 to 60 in the present invention.

Through tests of the examples 31~60, the result is shown in FIG. 7. In accordance with the formation weight of the biomembrane 20, the culture medium comprising 0.5% yeast extract, 2% $CaCO_3$, and 5% glucose can be an optimal medium to culture a biomembrane having a best production weight.

Examples 61~63

About 15 loops of *G. xylinus* subsp. *Xylinus* ATTC 10821, *G. xylinus* subsp. *Xylinus* ATTC 700187, and *G. Hansenii* ATCC 23769 are transferred from the slant culture to a sterile liquid medium (as the following Table 4). The liquid medium is cultured for 1~3 days at 37° C. by shaking, and then amplified with 2~30-folds sterile liquid medium. This amplification can be performed for 1~2 days in a fermenting tank or a shaking incubator so as to obtain seed culture for large-scaled production.

Figure 3:
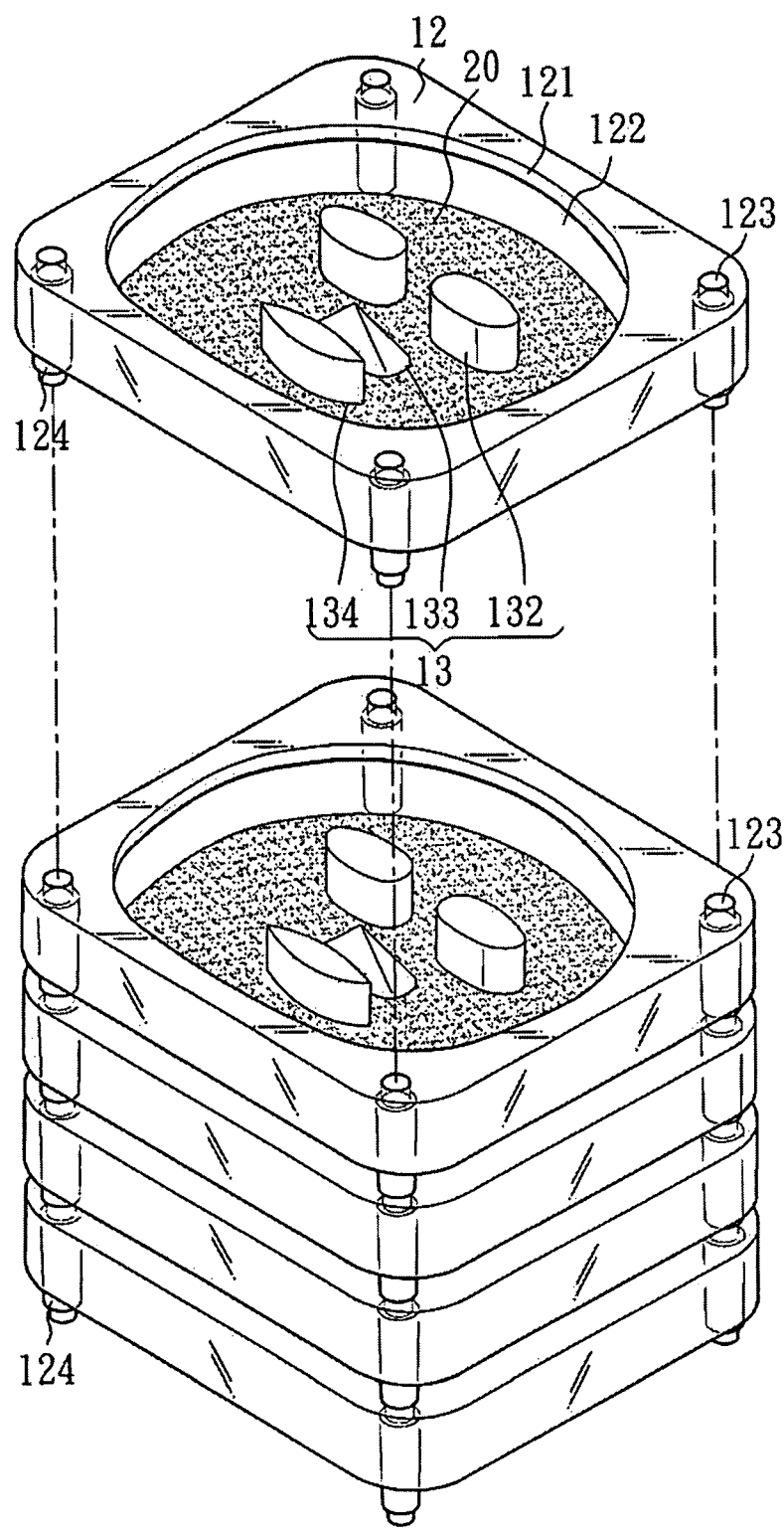
FIG. 3 is a perspective view of a container when production of a biomembrane occurs in the example of the present invention.

In the present examples, the container used therein is as shown in FIG. 3, and approximately is similar to the container shown in FIG. 2. However, the sidewall 12 of the container in the FIG. 3 has a recessive brink 121 at the upper part thereof, and a prominent brink 122 at the lower part thereof. Besides, the upper-portion cross-section of the pins 124 is greater than the cross-section of the holes 123.

About 1%~50% of the seed culture is mixed with the culture medium in Table 2 and that is cultured in the inner space of the above-mentioned container. Although FIG. 3 shows that the recessive brink 121 and the prominent brink 122 are placed in the inside of the sidewall 12, those also can be placed in the outside of the sidewall 12. Hence, the container can be vertically stacked up one by one through the recessive brink 121 and the prominent brink 122 correspondingly inserted with each other.

Besides, the container also can be vertically stacked up one by one as shown in FIG. 3. Through the pins 124 inserting into the holes 123, there is a vertical gap between neighboring containers. Hence, air can ventilate the container to promote the biomembrane growth. A biomembrane 20 is formed in a shape according to that of the container. At a constant temperature, the biomembrane 20 is cultured until the biomembrane 20 has a predetermined thickness. Then, the biomembrane 20 as shown in FIG. 5 is taken out.

TABLE 4

| Component | Content (%) |
| --- | --- |
| Glucose | 2 |
| Peptone | 1 |
| Yeast extract | 1 |
| $CaCO_3$ | 0.5 |
| $MgSO_4$ | 0.1 |

Example 64

About 1~5 loops of *X. campeastris* are transferred from the slant culture to a sterile liquid medium (as the following Table 5). The liquid medium is cultured for 1~3 days at 37° C. by shaking, and then amplified with 2~30-folds sterile liquid medium. This amplification can be performed for 1~2 days in a fermenting tank or a shaking incubator so as to obtain seed culture for large-scaled production.

TABLE 5

| Component | Content (%) |
| --- | --- |
| Glucose | 4 |
| Fructose | 2 |
| Peptone | 2 |
| Yeast extract | 2 |
| Citric acid | 0.2 |
| Potassium biphosphate | 0.2 |

Figure 4:
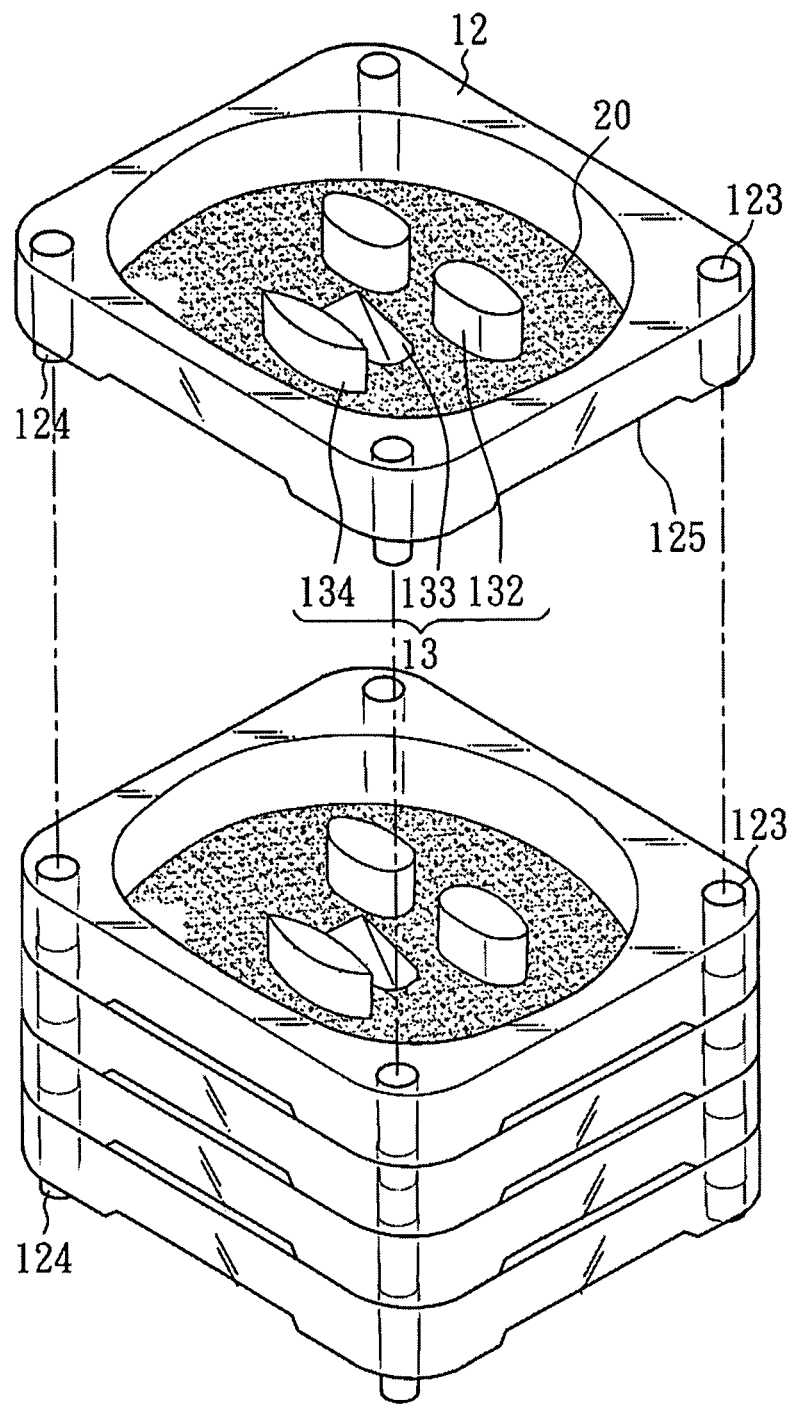
FIG. 4 is a perspective view of a container when production of a biomembrane occurs in the example of the present invention.

In the present examples, the container used therein is as shown in FIG. 4, and approximately is similar to the container shown in FIG. 2. However, the sidewall 12 has plural recesses 125 on the outer surface thereof. Besides, the recesses 125 are not limited to be formed on all the outer surface of the sidewall 12, but also can be formed on one, two, or three outer surfaces thereof.

About 1%~50% of the seed culture is mixed with the culture medium in Table 2 and that is cultured in the inner space of the above-mentioned container. Besides, the container also can be vertically stacked up one by one as shown in FIG. 3. Hence, air can ventilate the container to promote the biomembrane growth through the recesses 125. A biomembrane 20 is formed in a shape according to that of the container. At a constant temperature, the biomembrane 20 is cultured until the biomembrane 20 have a predetermined thickness. Then, the biomembrane 20 as shown in FIG. 5 is taken out.

Example 65

About 15 loops of *B. subtilis* var Natto are transferred from the slant culture to a sterile liquid medium (as Table 5 of Example 65). The liquid medium is cultured for 13 days at 37° C. by shaking, and then amplified with 2~30-folds sterile liquid medium. This amplification can be performed for 1~2 days in a fermenting tank or a shaking incubator so as to obtain seed culture for large-scaled production.

In the present examples, the containers used therein are as shown in FIGS. 1~4. About 1%~50% of the seed culture is mixed with the culture medium in Table 2 and that is cultured in the inner space of the above-mentioned containers. A biomembrane 20 is formed in a shape according to that of the container. The biomembrane 20 is cultured at a constant temperature until the biomembrane 20 has a predetermined thickness. Then, the biomembrane 20 as shown in FIG. 5 is taken out.

The biomembranes prepared above in Example 1~65 are pretreated with alkaline solution, and treated with acidic solution. Then, the biomembranes are processed by conventional steps for biomembranes in the field such as boiling, washing etc. and then subjected to following processes of making masks such as sterilization, addition of efficient compositions, packaging, marking, and so on. Hence, biological masks with efficient compositions can be formed.

During manufacturing, the biomembranes made by the method of the present invention are not required to change in shape by subsequent steps such as molding, cutting, and so forth. Furthermore, the biomembrane of the present invention does not have shortcomings of conventional masks being required to change in shape. Hence, the biomembrane in the present invention can have good yield without impairment due to the process of changing shape. Additionally, the cost of manufacturing can be economized due to not generating any waste.

Because of the specific embodiments illustrating the practice of the present invention, a person having ordinary skill in the art can easily understand other advantages and efficiency of the present invention through the content disclosed therein. The present invention can also be practiced or applied by other variant embodiments. Many other possible modifications and variations of any detail in the present specification based on different outlooks and applications can be made without departing from the spirit of the invention.

Although the present invention has been explained in relation to its preferred embodiment, it is to be understood that many other possible modifications and variations can be made without departing from the scope of the invention as hereinafter claimed.

What is claimed is:

1. A method for production of a biomembrane having a final shape, comprising the following steps:
    (a) providing a first medium and a microbial strain therein, and shaking them to form a seed culture;
    (b) putting the seed culture into containers having a second medium, and the containers comprising a bottom plate, a sidewall disposed on the bottom plate and surrounding and connecting the periphery of the bottom plate wherein plural holes are formed on an upper surface of the sidewall and plural pins corresponding to the holes are disposed on an lower surface of the sidewall, and at least one protrusion locating on the surface of the bottom plate to form an inner space, wherein at least two of the containers are correspondingly stacked by insertion of the pins of one container into the holes of the another container, and air flows between two of the containers for aerobic culture; and
    (c) culturing the seed culture in the containers until a biomembrane having a predetermined thickness is formed.

2. The method as claimed in claim 1, wherein the microbial strain is *Acetobacter* spp., *Gluconacetobacter* spp., *Xanthomonas* spp., or *Bacillus* spp.

3. The method as claimed in claim 2, wherein the microbial strain of the *Acetobacter* spp. is *A. xylinum*.

4. The method as claimed in claim 2, wherein the microbial strain of the *Gluconacetobacter* spp. is *G. xylinus* subsp. *xylinus*, or *G. hansenii*.

5. The method as claimed in claim 2, wherein the microbial strain of the *Xanthomonas* spp. is *X. camperastris*.

6. The method as claimed in claim 2, wherein the microbial strain of the *Bacillus* spp. is *B. subtilis* var Natto.

7. The method as claimed in claim 1, wherein the first medium and the second medium comprise a carbohydrate, an N-containing compound, a mineral, and a growth cofactor.

8. The method as claimed in claim 7, wherein the content of the carbohydrate, the N-containing compound, the mineral, and the growth cofactor is 1~30%, 0.1~6%, 0.05~3%, and 0.05~2%, respectively.

9. The method as claimed in claim 7, wherein at least one carbohydrate is selected from the group consisting of monosaccharide, disaccharides, polysaccharides, and carboxyl-containing compounds.

10. The method as claimed in claim 7, wherein at least one N-containing compound is selected from the group consisting of yeast extract, peptone, soybean powders, and gelatin.

11. The method as claimed in claim 7, wherein at least one mineral is selected from the group consisting of chloride salt, ammonium salt, sulfide salt, potassium salt, phosphate, magnesium salt, and sodium salt.

12. The method as claimed in claim 7, wherein at least one growth cofactor is selected from the group consisting of vitamin, nicotinic acid, citric acid, and the derivatives thereof.

13. The method as claimed in claim 7, further comprising a step (a1): amplifying the seed culture to afford great amount of seed culture for mass production after the step (a) is achieved.

14. The method as claimed in claim 1, wherein the sidewall has a recessive brink and a prominent brink, the recessive brink is at the upper part of the sidewall, and the prominent brink is at the lower part of the sidewall.

15. The method as claimed in claim 14, wherein the depth of the holes is less than or equal to the height of the pins.

16. The method as claimed in claim 14, wherein the area of the cross-section of the upper portion of the pins is greater than or equal to the area of the cross-section of the holes.

17. The method as claimed in claim 1, wherein plural recesses locate on an outer surface of the sidewall.

18. The method as claimed in claim 1, wherein the protrusion is columnar, taper, or sheeted and forms at least one void space in the biomembrane.

19. The method as claimed in claim 1, wherein the shape of the sidewall surrounding the periphery of the bottom plate is circular, elliptic, polygonal, irregular, or oval and wherein there are four protrusions arranged in a facial pattern corresponding to eyes, mouth and nose for a human facial mask.

20. The method as claimed in claim 19, wherein the biomembrane forms an intregal human facial mask which is removed from the container.

* * * * *